United States Patent
Marash et al.

(10) Patent No.: US 9,227,087 B2
(45) Date of Patent: *Jan. 5, 2016

(54) TELETHERAPY CONTROL SYSTEM AND METHOD

(75) Inventors: Michael Marash, Rishon Le'tzion (IL); Guy Lavi, Mishmeret (IL)

(73) Assignee: P-CURE Ltd., Lod (IL)

( * ) Notice: Subject to any disclaimer, the term of this patent is extended or adjusted under 35 U.S.C. 154(b) by 224 days.

This patent is subject to a terminal disclaimer.

(21) Appl. No.: 13/813,956

(22) PCT Filed: Jul. 31, 2011

(86) PCT No.: PCT/IL2011/000618
§ 371 (c)(1),
(2), (4) Date: Feb. 4, 2013

(87) PCT Pub. No.: WO2012/017427
PCT Pub. Date: Feb. 9, 2012

(65) Prior Publication Data
US 2013/0163724 A1 Jun. 27, 2013

Related U.S. Application Data

(60) Provisional application No. 61/370,480, filed on Aug. 4, 2010.

(51) Int. Cl.
*A61B 6/00* (2006.01)
*A61N 5/10* (2006.01)
*G06T 7/00* (2006.01)

(52) U.S. Cl.
CPC ............ *A61N 5/1064* (2013.01); *A61B 6/5235* (2013.01); *A61N 5/103* (2013.01);
(Continued)

(58) Field of Classification Search
CPC ....... A61N 5/00; A61N 5/103; A61N 5/1038; A61N 5/1039; A61N 5/1048; A61N 5/1049; A61N 5/1064; A61N 5/1069; A61N 5/1075; A61B 6/00; A61B 6/02; A61B 6/022; A61B 6/03; A61B 6/04; A61B 6/42; A61B 6/48; A61B 6/488; A61B 6/52; A61B 6/5211; A61B 6/5223; A61B 6/5229; A61B 6/5235; A61B 6/58; A61B 6/589; G06T 7/00; G06T 7/0012; G06T 7/0014
USPC ...................... 378/4, 8, 20, 62, 65, 68, 91, 95, 378/162–165, 204, 205, 210, 901; 382/128, 382/131, 217–219
See application file for complete search history.

(56) References Cited

U.S. PATENT DOCUMENTS 7,405,407 B2 * 7/2008 Hiramoto et al. ........ 250/370.09
7,587,023 B2 * 9/2009 Hur ................................ 378/16
(Continued)

FOREIGN PATENT DOCUMENTS

WO 2005/024721 A2 3/2005
WO WO 2010113050 A2 * 10/2010 .............. G06F 19/00

OTHER PUBLICATIONS

International Search Report for PCT/IL2011/000618 mailed Nov. 29, 2011, European Patent Office.
(Continued)

*Primary Examiner* — Anastasia Midkiff
(74) *Attorney, Agent, or Firm* — Simon Kahn; Chanoch Kahn

(57) ABSTRACT

A teletherapy control system constituted of: a teletherapy management server; and a computerized tomography unit in communication with the teletherapy management server, the teletherapy management server arranged to: obtain at least one reference image of a target area; obtain from the computerized tomography unit at least one scout image of the target area; compare the obtained at least one scout image of the target area with the obtained at least one reference image of the target area; identify the location coordinates of the target area responsive to the comparison of the obtained scout image with the obtained at least one reference image; and output a control signal to a positioning device responsive to the identified location coordinates of the target area.

12 Claims, 2 Drawing Sheets

(52) U.S. Cl.
CPC ............ *G06T 7/0012* (2013.01); *G06T 7/0014* (2013.01); *A61B 6/488* (2013.01); *A61B 6/545* (2013.01); *A61B 6/589* (2013.01); *A61N 5/1049* (2013.01); *A61N 5/1069* (2013.01); *A61N 2005/1062* (2013.01); *A61N 2005/1074* (2013.01); *G06T 7/0044* (2013.01); *G06T 2207/10072* (2013.01); *G06T 2207/10081* (2013.01); *G06T 2207/10124* (2013.01); *G06T 2207/30004* (2013.01)

(56) References Cited

U.S. PATENT DOCUMENTS

| | | | |
|---|---|---|---|
| 8,755,489 B2* | 6/2014 | Lavi et al. | 378/65 |
| 2004/0005027 A1* | 1/2004 | Nafstadius | 378/65 |
| 2007/0003123 A1 | 1/2007 | Fu | |
| 2007/0041494 A1* | 2/2007 | Ruchala et al. | 378/65 |
| 2007/0127792 A1* | 6/2007 | Virtue | 382/128 |
| 2007/0238963 A1* | 10/2007 | Kaminaga et al. | 600/407 |
| 2008/0002809 A1* | 1/2008 | Bodduluri | 378/41 |
| 2008/0253639 A1* | 10/2008 | Van Den Brink | 382/131 |
| 2009/0087124 A1 | 4/2009 | Nord | |
| 2009/0147909 A1* | 6/2009 | Yoda et al. | 378/4 |
| 2010/0119032 A1* | 5/2010 | Yan et al. | 378/4 |
| 2012/0035463 A1* | 2/2012 | Pekar et al. | 600/411 |

OTHER PUBLICATIONS

Written Opinion of the International Searching Authority for PCT/IL2011/000618 mailed Nov. 29, 2011, European Patent Office.

First office action for CN201180047174.8 mailed Dec. 29, 2014 for parallel China Application—Translated summary and complete action in Chinese.

* cited by examiner

TELETHERAPY CONTROL SYSTEM AND METHOD

BACKGROUND OF THE INVENTION

The invention relates generally to the field of teletherapy and in particular to a system and method for identifying a patient location within a treatment room utilizing a scout image of a computerized tomography scanner.

Teletherapy is defined as a treatment methodology in which an irradiation source is at a distance from the body to be treated. X-rays and electron beams have long been used in teletherapy to treat various cancers. Unfortunately, X-rays and electron beams exhibit a linear energy transfer approaching an exponential attenuation function, and are therefore of minimal use for deeply embedded growths. Recently, the use of heavy particles, particularly hadrons, in teletherapy has found increasing acceptance, due to the ability of heavy particles to penetrate to a specific depth without appreciably harming intervening tissue. In particular, the linear energy transfer of hadrons exhibits an inversed depth profile with a marked Bragg peak defined as the point at which the hadrons deposit most of their energy, and occurs at the end of the hadrons path. As a result of this effect, increased energy can be directed at an embedded growth as compared to X-rays and electron beams, which particularly harm intervening tissues. While the term hadrons include a wide range of particles, practically, protons and various ions are most widely used in therapy.

Pre-treatment imaging is an important part of teletherapy and is particularly important in obtaining precise location information of the patient as well as updated information regarding the diseased tissue to be irradiated. Location information of the patient is required for accurate positioning of the patient in relation to the irradiation beam.

Prior art methods of pre-treatment imaging exist based on x-ray technology, wherein an x-ray image, or a pair of orthogonal x-ray images, is taken of an immobilized patient in position for irradiation. The x-ray image, or a pair of orthogonal images, is compared with synthetic x-ray images derived from a reference computerized tomography (CT) scan used for initial treatment planning, and any location adjustments are performed. The synthetic x-ray image is often called a digital reconstructed radiograph (DRR).

Commercially available CT units are typically arranged to display or otherwise output a scout image, wherein the CT unit provides a quickly acquired x-ray projection, which is used in the prior art to both prescribe desired CT slices, and/or to provide a complete three dimensional image of a selected area, which is typically finely selected responsive to the scout image. Thus a scout image is a planar image or a curved-planar image of a patient created by a CT unit. CT units provide scout images based on a number of scout generation technologies, including, but not limited to: a moving fan-beam shaped single detector row geometry; a single static fan-beam shaped multi-detector row geometry; and a moving fan-beam shaped multi-detector row geometry.

An in-room CT, wherein a CT unit is provided within a teletherapy treatment room co-located with teletherapy equipment, has been proposed as providing extremely accurate positioning and continued anatomical volume imaging thus allowing for frequent treatment plan updates. Unfortunately, a CT scan exposes the patient to a very large radiation dose, which is not desirable on a regular basis. Furthermore a CT scan is time consuming and thus reduces the throughput of the teletherapy treatment room.

The layout of a teletherapy treatment room is a major expense, and the equipment required for proper operation must be selected and carefully placed so as to maximize throughput. In particular, any equipment utilized in identifying precise patient location must be arranged to be at known coordinates, or at a controlled range of coordinates, in relation to the irradiation source.

SUMMARY OF THE INVENTION

Accordingly, it is a principal object of the present invention to overcome at least some of the disadvantages of present and prior art methods of teletherapy control. In one embodiment this is provided by a teletherapy control system comprising: a teletherapy management server; and a computerized tomography unit in communication with the teletherapy management server. The teletherapy management server is arranged to: obtain at least one reference image of a target area; obtain from the computerized tomography unit at least one scout image of the target area; compare the obtained at least one scout image of the target area with the obtained at least one reference image of the target area; identify the location coordinates of the target area responsive to the comparison of the obtained scout image with the obtained at least one reference image; and output a control signal to a positioning device responsive to the identified location coordinates of the target area.

In one further embodiment the teletherapy control system further comprises the positioning device. The positioning device is in communication with the teletherapy management server.

In one further embodiment the obtained at least one reference image is a synthetic image derived from a complete computerized tomography scan. In one further embodiment the teletherapy management server generates the obtained at least one reference image from the complete computerized tomography scan.

In one further embodiment the obtained at least one reference image is a digital reconstructed radiograph, preferably obtained as part of a treatment planning session. In another further embodiment the obtained at least one reference image is a reference scout image stored on a memory in communication with the teletherapy management server.

In another further embodiment, the obtained at least one reference image comprises a plurality of reference scout images of differing perspectives stored on a memory in communication with the teletherapy management server, the plurality of scout images representing a first set of views. The teletherapy management server is arranged to operate the computerized tomography unit to obtain a plurality of scout images of the target area of differing perspectives, the plurality of scout images of the target area representing a second set of views. The first set of views are compared with the second set of views.

In another further embodiment, the obtained at least one reference image comprises a plurality of orthogonal reference scout images stored on a memory in communication with the teletherapy management server. The teletherapy management server is arranged to operate the computerized tomography unit to obtain a plurality of orthogonal scout images of the target area which are compared with the plurality of orthogonal reference scout images.

Independently, certain embodiments provide for a method of controlling a teletherapy system, the method comprising: obtaining at least one reference image of a target area; obtaining at least one scout image of the target area by a CT unit; comparing the obtained at least one scout image of the target area with the obtained at least one reference image; identifying the location coordinates of the target area responsive to the comparison of the obtained scout image with the obtained at least one reference image; and controlling a positioning device responsive to the identified location coordinates.

In one further embodiment the obtained at least one reference image is a digital reconstructed radiograph, preferably obtained as part of a treatment planning session. In another further embodiment the obtained at least one reference image is a synthetic image derived from a complete computerized tomography scan.

In another further embodiment the obtaining of the at least one reference image comprises: retrieving a complete computerized tomography scan; and generating a synthetic image from the retrieved complete computerized tomography scan. In another further embodiment the reference image is a reference scout image.

In another further embodiment, the obtained at least one reference image comprises a plurality of reference scout images of differing perspectives, the plurality of scout images representing a first set of views. The obtaining at least one scout image comprises obtaining a plurality of scout images of the target area of differing perspectives, the plurality of scout images of the target area representing a second set of views. The comparing comprises comparing the first set of views with the second set of views.

In another further embodiment, the obtained at least one reference image comprises a plurality of orthogonal reference scout images. The obtaining at least one scout image comprises obtaining a plurality of orthogonal scout images of the target area and the comparing comprises comparing the plurality of orthogonal reference scout images with the plurality of orthogonal scout images of the target area.

Independently, in certain embodiments a computer readable medium containing instructions for controlling an electronic device to perform a method of controlling a teletherapy system is provided, the method comprising obtaining at least one reference image; obtaining at least one scout image of a target area by a computerized tomography unit; comparing the obtained at least one scout image of the target area with the obtained at least one reference image; and controlling a positioning device responsive to the comparison of the obtained scout image with the obtained at least one reference image.

In one further embodiment the obtained at least one reference image is a synthetic image derived from a complete computerized tomography scan. In another further embodiment the obtaining at least one reference image comprises: retrieving a complete computerized tomography scan; and generating a synthetic image from the retrieved complete computerized tomography scan.

In one further embodiment the obtained at least one reference image is a reference scout image. In another further embodiment the obtained at least one reference image comprises a plurality of reference scout images of differing views, said plurality of reference scout images representing a first set of views; said obtaining at least one scout image of the target area comprises obtaining a plurality of scout images of the target area of differing views, said plurality of scout images of the target area representing a second set of views; and wherein said comparing comprises comparing the first set of views with the second set of views.

In one further embodiment the obtained at least one reference image comprises a plurality of orthogonal reference scout images; said obtaining at least one scout image of the target area comprises obtaining a plurality of orthogonal scout images of the target area; and wherein said comparing comprises comparing the plurality of orthogonal reference scout images with the plurality of orthogonal scout images of the target area.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

Figure 1:
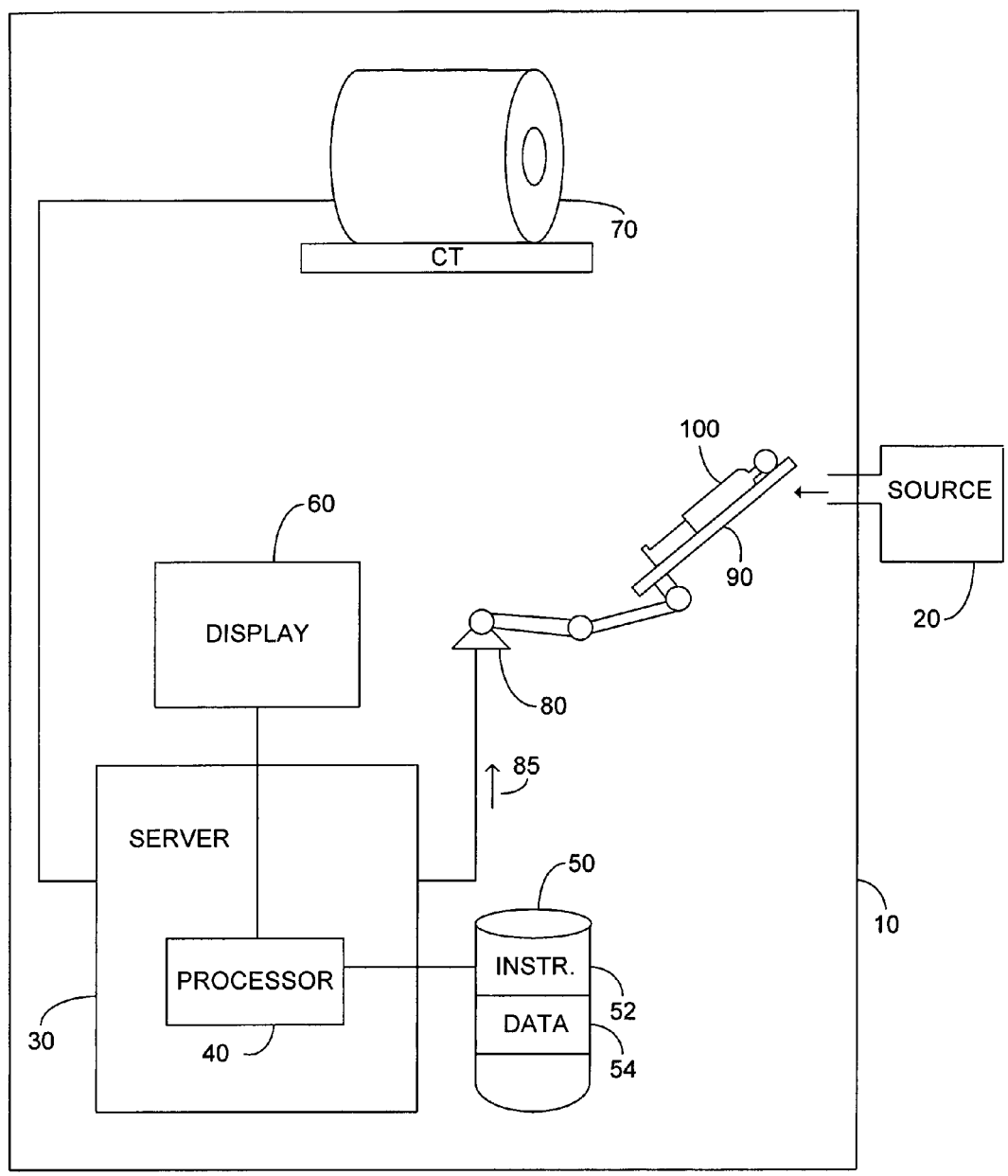
FIG. 1 illustrates a high level block diagram of an exemplary embodiment of an irradiation treatment room comprising a teletherapy management server, a CT unit, and a positioning apparatus.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting. The term target area as used herein refers to any target area, including without limitation a total patient view.

FIG. 1 illustrates a high level block diagram of an exemplary embodiment of an irradiation treatment room 10 comprising: a therapeutic agent source 20; a teletherapy management server 30 comprising a processor 40; a memory 50; a display 60; a CT unit 70: and a positioning apparatus 80 responsive to a control signal 85 and in communication with a patient platform 90 having thereon a patient 100. Therapeutic agent source 20 is illustrated as a fixed beam irradiation source, without limitation, and may be replaced with a gantry or other therapeutic agent source without exceeding the scope. Processor 40 is in electronic communication with each of memory 50 and display 60, and is particularly arranged to read computer readable instructions stored on a first portion 52 of memory 50 and read image data received at a treatment planning phase from a second portion 54 of memory 50. Teletherapy management server 30 is in electrical communication with CT unit 70 and is further in electrical communication with positioning apparatus 80. Positioning apparatus 80 is arranged to position patient 100 immobilized to patient platform 90 to a particular position in relation to therapeutic agent source 20, the particular position obtained responsive to teletherapy management server 30. Teletherapy management server 30 is illustrated as a single unit, and may be composed of a plurality of processing units in intercommunication as required, without exceeding the scope.

In operation, a CT scan is performed on a patient 100, typically at a planning station, to generate a reference image of a target area. The reference image may comprise any of: a complete CT scan, a DRR derived from the complete CT scan, a scout image, a plurality of scout images and a plurality of orthogonal scout images. There is no limitation to the reference image source, and CT unit 70 may be utilized without limitation. In particular, CT unit 70 may be periodically utilized to perform a full CT scan of patient 100 for follow up and therapy plan adjustments, with periodicity of a full CT scan being less than the periodicity of treatment. The reference image, from whatever source, is stored on second portion 54 of memory 50. Furthermore, scout images obtained from CT unit 70, as described below, are preferably further stored on second portion 54 of memory 50, and in one embodiment are compared with each other to identify changes in target tissue. In another embodiment, the CT scan is stored on second portion 54 of memory 50 and processor 40 is arranged to generate the DRR from the stored CT scan.

Teletherapy management server 30 is further arranged at a treatment session, wherein a full CT scan is not to be performed, to obtain a scout image of patient 100 via CT unit 70, particularly of the target area. As indicated above the target area may comprise a complete patient view, without limitation. Advantageously, obtaining a scout image exposes patient 100 to significantly reduced radiation as compared to a full CT scan. Preferably, patient 100 is first immobilized to patient platform 90 in the desired position for teletherapy, and the scout image is obtained for patient 100 while so immobilized. In one non-limiting embodiment positioning apparatus 80 is further arranged, preferably responsive to teletherapy management server 30, to transport patient platform 90 towards an imaging area of CT unit 70 so as to enable the scout image to be obtained. In one non-limiting embodiment, positioning apparatus 80 is operative responsive to teletherapy management server 30, particularly responsive to control signal 85. There is no requirement that communication between teletherapy management server 30 and positioning apparatus 80 be unidirectional, and bidirectional communication is particularly contemplated. Advantageously, the position of patient 100 is well defined in relation to patient platform 90, and the position of patient platform 90 is precisely defined to teletherapy management server 30.

Teletherapy management server 30 obtains from CT unit 70 at least one scout image. In one non-limiting embodiment two or more orthogonal scout images are obtained. In another non-limiting embodiment two or more scout images are obtained. Preferably, CT unit 70 is arranged, responsive to commands received from teletherapy management server 30, to provide the one or more scout images.

Processor 40 of teletherapy management server 30 is further arranged to retrieve from second portion 54 of memory 50 the reference image, or images, described above, and compare the obtained one or more scout images to the retrieved reference image. In an exemplary embodiment one or more scout images obtained from CT unit 70 are compared with the DRR derived from the CT scan at the treatment planning stage, or the DRR derived from a periodic full CT scan, as described above, and stored on second portion 54 of memory 50.

Responsive to the comparison of the one or more scout images to the reference image, or images, location coordinates of the target area within irradiation treatment room 10 are identified. In one embodiment, positioning errors are identified. Preferably position correction instructions are transmitted to positioning apparatus 80 responsive to the identified location coordinates. Positioning apparatus 80 is arranged, responsive to the transmitted instructions, to adjust the patient positioning accordingly. In one embodiment, the positioning device is positioned responsive to the identified positioning errors.

In one non-limiting embodiment, in the event that a full CT scan is performed periodically by CT unit 70, the full CT scan and the scout image obtained at the time of the full CT scan are further utilized to perform volumetric based alignment after comparison with the full CT scan of the treatment planning stage stored on second portion 54 of memory 50.

Teletherapy management server 30 is further arranged to command positioning apparatus 80 to position patient platform 90 at a precise position in relation to therapeutic agent source 20, prior to providing the therapeutic agent. Teletherapy management server 30 optionally further provides the therapeutic agent from therapeutic agent source 20, responsive to a communication path (not shown) between therapeutic agent source 20 and teletherapy management server 30.

Figure 2:
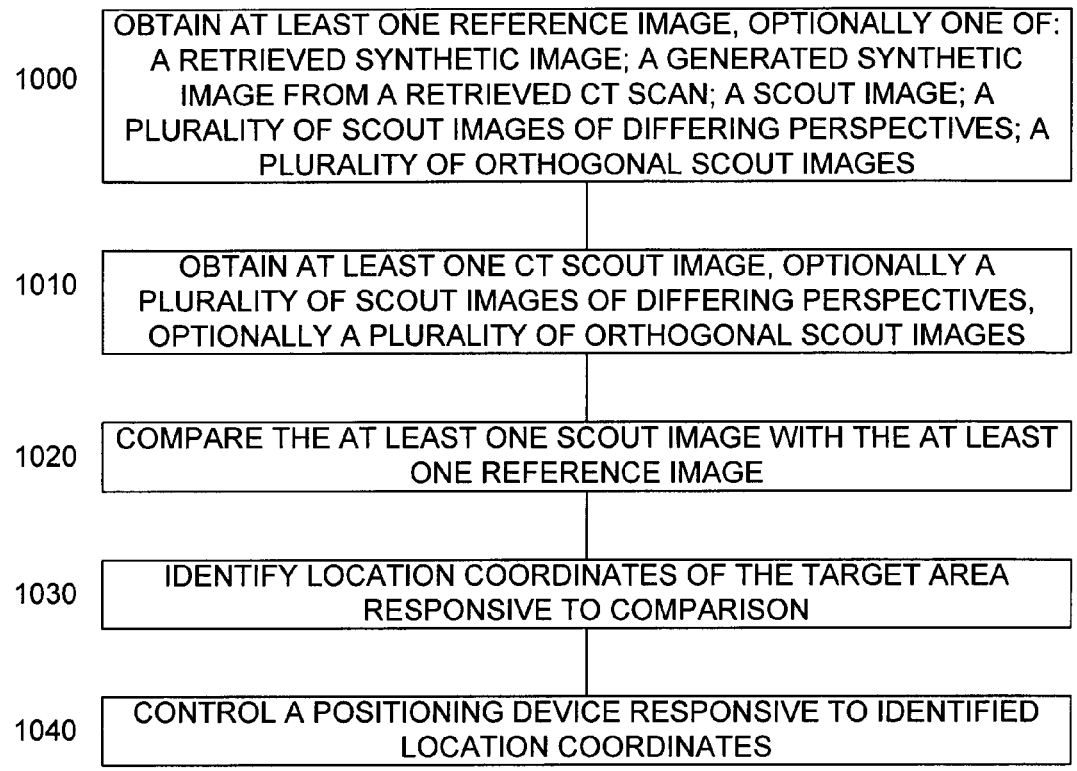
FIG. 2 illustrates a high level flow chart of the method of operation of the teletherapy management server of FIG. 1.

FIG. 2 illustrates a high level flow chart of the method of operation of teletherapy management server 30 of FIG. 1, in accordance with computer readable instructions stored on first portion 52 of memory 50. In stage 1000, at least one reference image is obtained, preferably of a target area. In one embodiment the reference is at least one retrieved synthetic image stored on second portion 54 of memory 50. In another embodiment the reference image is a reference CT scan, and processor 40 is further arranged to render at least one synthetic image from the retrieved CT scan. In another embodiment the obtained at least one reference image comprises a scout image. In another embodiment the obtained at least one reference image comprises a plurality of scout images. In another embodiment the obtained at least one reference image comprises a plurality of orthogonal scout images.

In stage 1010, a CT scout image is obtained, preferably from CT unit 70, and preferably of the target area, which in an exemplary embodiment comprises an entire patient view. A plurality of scout images, preferably orthogonal scout images, of differing perspectives, may be obtained. The images are preferably of planes consonant with image planes of the reference image of stage 1000.

In stage 1020, the obtained reference image, or images, of stage 1000 are compared with the obtained scout image, or images, of stage 1010. In one particular embodiment the at least one reference image of stage 1000 comprises a plurality of reference scout images of differing perspectives, thus representing a first set of views, and the scout image of stage 1010 comprises a plurality of scout images of differing perspectives, thus representing a second set of different views. Preferably the differing perspectives are of consonant planes. In one particular embodiment the at least one reference image of stage 1000 comprises a plurality of orthogonal reference scout images, thus representing a first set of views, and the scout image of stage 1010 comprises a plurality of orthogonal scout images, thus representing a second set of different views. Preferably the differing orthogonal images are of consonant planes. In stage 1030, the location coordinates of the target area within the treatment room are identified responsive to the comparison of stage 1020. In one embodiment, positioning errors are identified. In stage 1040, a positioning device, such as positioning apparatus 80, is controlled responsive to the identified location coordinates of stage 1030. In one embodiment, the positioning device is positioned responsive to the identified positioning errors.

Figure 3:
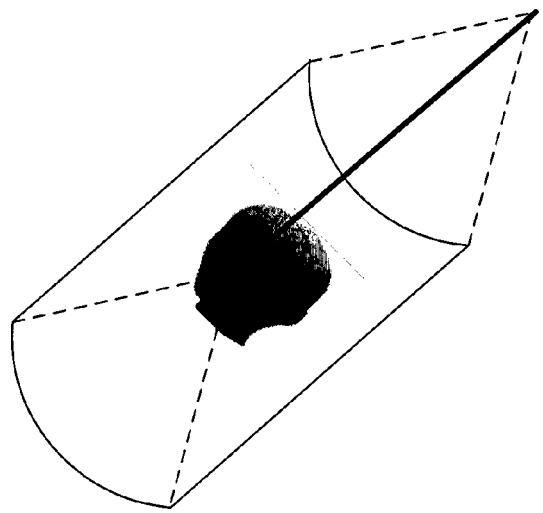
FIG. 3 illustrates a high level diagram of a scout image.

FIG. 3 illustrates a high level diagram of a scout image. The geometry of a scout image depends on the shape of the detector array as well as on the number of detector rows of CT unit 70. FIG. 3 shows the geometry of a scout image for a single row fan beam projection. The curved surface is formed by a continuous motion of the single row of detectors along the patient. The constant movement of patient platform 90 with patient 100 immobilized thereon is equivalent to an opposite but similar motion of the x-ray source and the detector row along patient 100. The bold line thus represents the virtually moving x-ray source while the curved surface represents the virtually moving detector row.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

We claim:

1. A teletherapy control system comprising:
 a teletherapy management server; and
 a computerized tomography unit in communication with said teletherapy management server,
 said teletherapy management server arranged to:
  perform a complete computerized tomography scan of the target area thereby exposing the target area to a first amount of radiation;
  obtain a first reference image of a target area, said first reference image derived from said performed complete computerized tomography scan;
  control said computerized tomography unit to perform a first scout image scan of the target area thereby exposing the target area to a second amount of radiation, the second amount of radiation significantly less than the first amount of radiation;
  obtain from said computerized tomography unit a first scout image of the target area responsive to said performed first scout image scan;
  compare the obtained first scout image of the target area with the obtained first reference image of the target area;
  identify the location coordinates of the target area responsive to the comparison of the obtained first scout image with the obtained first reference image; and
  output a control signal to a positioning device responsive to the identified location coordinates of the target area.

2. The teletherapy control system according to claim 1, further comprising said positioning device, said positioning device in communication with said teletherapy management server.

3. The teletherapy control system according to claim 1, wherein the obtained first reference image is a synthetic image derived from the performed complete computerized tomography scan.

4. The teletherapy control system according to claim 1, wherein the obtained first reference image is stored on a memory in communication with said teletherapy management server.

5. The teletherapy control system according to claim 1, wherein said teletherapy management server is further arranged to:
 obtain a second reference image of the target area, said second reference image derived from said performed complete computerized tomography scan and orthogonal to said obtained first reference image;
 control said computerized tomography unit to perform a second scout image scan of the target area, thereby exposing the target area to a third amount of radiation, the third amount of radiation significantly less than the first amount of radiation, said second scout image scan orthogonal to said first scout image scan, and obtain from said computerized tomography unit a second scout image of the target area responsive to said performed second scout image scan; and
 compare the obtained second scout image of the target area with the obtained second reference image of the target area,
 wherein said identification of the location coordinates is further responsive to the comparison of the obtained second scout image with the obtained second reference image.

6. A method of controlling a teletherapy system, the method comprising:
 performing a complete computerized tomography scan of the target area via a computerized tomography unit thereby exposing the target area to a first amount of radiation;
 obtaining a first reference image the target area, said first reference image derived from said performed complete computerized tomography scan;
 performing a first scout image scan of the target area via the computerized tomography unit thereby exposing the target area to a second amount of radiation, the second amount of radiation significantly less than the first amount of radiation;
 obtaining a first scout image of the target area responsive to said performed first scout image scan;
 comparing the obtained first scout image of the target area with the obtained first reference image;
 identifying the location coordinates of the target area responsive to the comparison of the obtained first scout image with the obtained first reference image; and controlling a positioning device responsive to the identified location coordinates.

7. The method according to claim 6, wherein the obtained first reference image is a synthetic image derived from the performed complete computerized tomography scan.

8. The method according to claim 6, further comprising:
obtaining a second reference image of the target area, said second reference image derived from said performed complete computerized tomography scan and orthogonal to said obtained first reference image;
performing a second scout image scan of the target area, thereby exposing the target area to a third amount of radiation, the third amount of radiation significantly less than the first amount of radiation, said second scout image scan orthogonal to said first scout image scan, and obtaining from said computerized tomography unit a second scout image of the target area responsive to said performed second scout image scan; and
comparing the obtained second scout image of the target area with the obtained second reference image of the target area,
wherein said identifying of the location coordinates is further responsive to the comparison of the obtained second scout image with the obtained second reference image.

9. A computer-readable medium containing instructions for controlling an electronic device to perform a method of controlling a teletherapy system, the method comprising:
performing a complete computerized tomography scan of the target area via a computerized tomography unit thereby exposing the target area to a first amount of radiation;
obtaining a first reference image the target area, said first reference image derived from a complete computerized tomography scan performed by a computerized tomography unit and associated with exposure of a first amount of radiation;
performing a first scout image scan of the target area by the computerized tomography unit thereby exposing the target area to a second amount of radiation, the second amount of radiation significantly less than the first amount of radiation;
obtaining a first scout image of the target area responsive to said performed first scout image scan;
comparing the obtained first scout image of the target area with the first reference image;
identifying the location coordinates of the target area responsive to the comparison of the obtained first scout image with the obtained first reference image; and
controlling a positioning device responsive to the identified location coordinates and to the comparison of the obtained first scout image with the obtained first reference image.

10. The computer-readable medium according to claim 9, wherein the obtained first reference image is a synthetic image derived from the complete computerized tomography scan.

11. The computer-readable medium according to claim 9, wherein said obtaining at least one reference image comprises:
retrieving data regarding the performed computerized tomography scan; and
generating a synthetic image from the retrieved complete computerized tomography scan data.

12. The computer-readable medium according to claim 9, further comprising:
obtaining a second reference image of the target area, said second reference image derived from said performed complete computerized tomography scan and orthogonal to said obtained first reference image;
performing a second scout image scan of the target area, thereby exposing the target area to a third amount of radiation, the third amount of radiation significantly less than the first amount of radiation, said second scout image scan orthogonal to said first scout image scan, and obtaining from said computerized tomography unit a second scout image of the target area responsive to said performed second scout image scan; and
comparing the obtained second scout image of the target area with the obtained second reference image of the target area,
wherein said controlling the positioning device is further responsive to said comparing the obtained second scout image of the target area with the obtained second reference image of the target area.

* * * * *